United States Patent [19]

Stewart

[11] 4,286,466

[45] Sep. 1, 1981

[54] METHOD AND APPARATUS FOR PNEUMATICALLY SAMPLING POWDERS

[75] Inventor: Ralph J. Stewart, Boulder, Colo.

[73] Assignee: International Business Machines Corporation, Armonk, N.Y.

[21] Appl. No.: 83,067

[22] Filed: Oct. 9, 1979

[51] Int. Cl.³ .............................................. G01N 1/14
[52] U.S. Cl. .............................. 73/863.83; 73/864.33
[58] Field of Search .............. 73/421 R, 421 B, 422 R

[56] References Cited

U.S. PATENT DOCUMENTS

| | | | |
|---|---|---|---|
| Re. 29,087 | 12/1976 | Larson . | |
| 3,156,120 | 11/1964 | Kowynia | 73/421 B |
| 3,438,261 | 4/1969 | Collins | 73/422 R |
| 3,782,200 | 1/1974 | Maas . | |
| 3,869,921 | 3/1975 | Irwin . | |
| 3,880,011 | 3/1975 | Johnson | 73/421 B |
| 3,901,087 | 8/1975 | Fabritus | 73/421 B |
| 3,973,440 | 8/1976 | Vande Ven | 73/421 B |

Primary Examiner—S. Clement Swisher

Attorney, Agent, or Firm—Francis A. Sirr

[57] ABSTRACT

A pneumatic sampler for use in collecting a sample of xerographic toner from a mass of such toner. A positive-pressure air source is connected to atmosphere through a venturi so as to produce a negative-pressure source. The positive-pressure source is also adapted to be connected through a first conduit to the toner mass. Positive-pressure airflow through this first conduit both purges the first conduit of residual toner and fluidizes at least a portion of the toner mass. A toner sample container is adapted to be simultaneously connected through a second conduit to the venturi. The resulting negative-pressure airflow through the second conduit evacuates the container. Negative-pressure induced airflow also purges the second conduit of residual toner. The container is connected to the toner mass through the series-connected and now-purged first and second conduits, and the negative-pressure within the container produces flow of toner from the toner mass to the container.

11 Claims, 7 Drawing Figures

VALVE POSITION 1

VALVE POSITION 2

METHOD AND APPARATUS FOR PNEUMATICALLY SAMPLING POWDERS

TECHNICAL FIELD

This invention relates to the sampling of particulate material, and finds particular utility in the sampling very fine, and thus possibly explosive, powders, such as toner which is to be used in xerographic devices.

BACKGROUND ART

Prior known sample collectors are exemplified by the following patents. U.S. Pat. No. Re. 29,087 discloses a particulate material sampling device wherein a hollow-probe is lowered into a grain sample, whereupon a vacuum pump causes grain to flow into a hole in the probe and through a hose into a sample container. Such arrangements provide no means to purge the walls of the probe or hose between samples. Also, such arrangements include an airflow filter which allows the smallest sample particles to pass through the filter, into the vacuum pump. Thus, a non-representative sample is obtained, especially when the intent of the sampler is to determine particle size distribution. Such particle carry-over into the pump may be detrimental to the pump.

U.S. Pat. No. 3,869,921 is exemplary of liquid sampling wherein an intake chamber is first immersed in a mass of liquid to be sampled. A pneumatic timer then cyclically operates to initiate a sampling internal by virtue of a low-pressure circuit. Operation of this timer controls a high-pressure circuit which is operative to pressurize the intake chamber and thereby force a liquid sample from this chamber to a sample container. Here again, no attempt is made to avoid contamination of a sample by a prior sample and this arrangement is not suitable for use with particulate material.

U.S. Pat. No. 3,782,200 samples flowing particulate material by means of a collecting tube having an opening in a wall thereof facing the flow path to be sampled. A piston moves in the collecting tube. One direction of piston movement evacuates the tube's particulate material to a position downstream of the tube, while subsequent movement of the piston, in the opposite direction, causes fresh material now collected in the tube to be dispensed to a sampling area. This arrangement is exemplary of sampling schemes requiring mechanical movement of a sample device, with attendant wear and contamination which are particularly associated with fine powders. In this arrangement the mechanical handling, and the energy expended in moving the sample may alter the sample's characteristics.

SUMMARY OF THE INVENTION

The present invention is unique in that a pneumatically operated sampler operates with a source of positive pressure to purge the sample conduit of prior sampling material, while at the same time evacuating a sample container, and then subsequently collects a sample by connecting the now-evacuated sample container to a mass to be sampled, such connection being exclusively by way of the now-purged sample conduit.

While the present invention is described in the environment of toner sampling, it is not to be limited thereto. For example, a solid-liquid slurry could be sampled, with the limitation that the solid be no larger than the various conduit and valve flow areas.

With the present invention there is no loss of sample due to venting or filtering, as is typically found in sampler systems employing positive pressure air assist, and in systems employing a vacuum pump. A fine-powder sampler cannot tolerate sample loss.

The foregoing and other features of this invention, as well as its advantages and applications, will be apparent from the following detailed description of the preferred embodiments which are illustrated in the accompanying drawing.

DESCRIPTION OF THE PREFERRRED EMBODIMENTS

Figure 1:
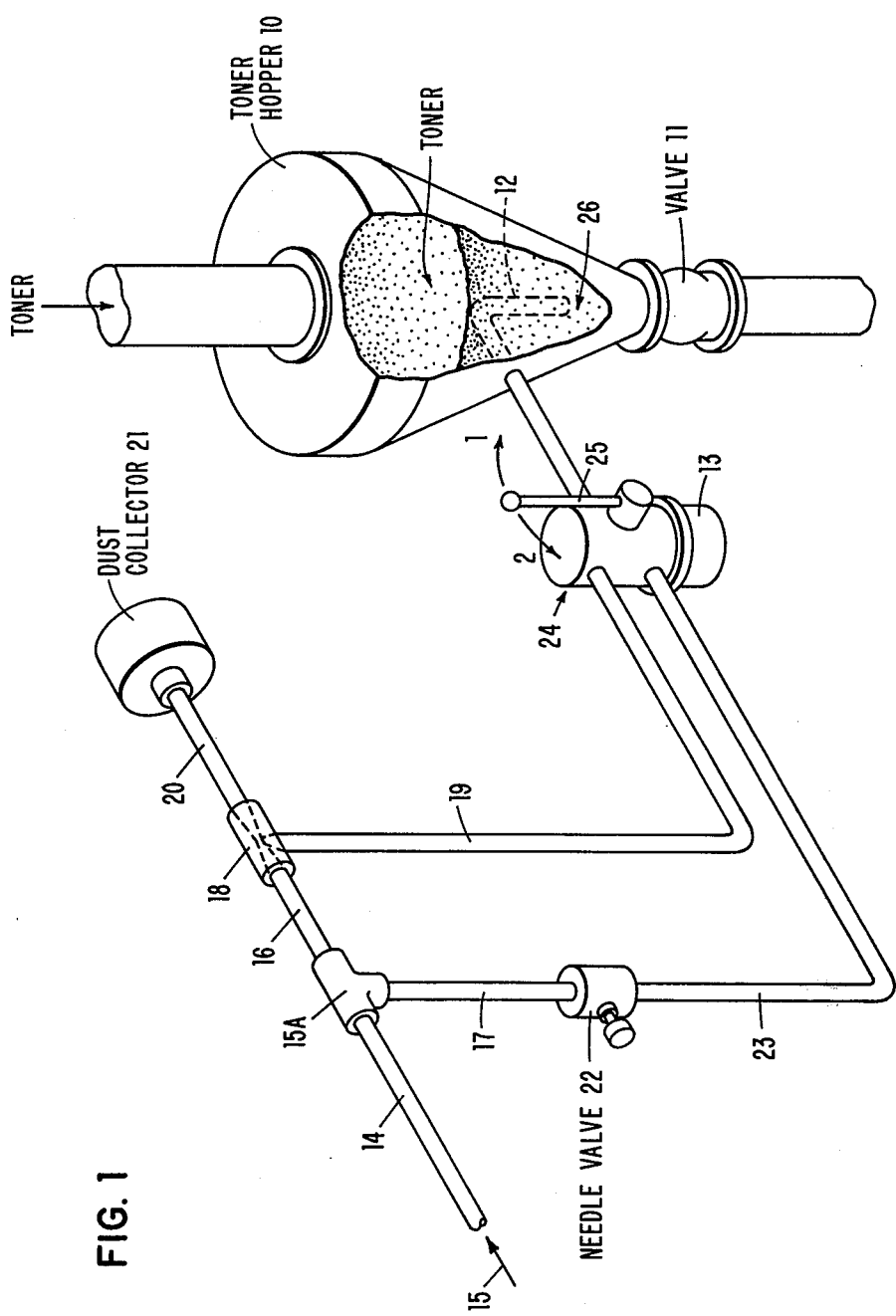
FIG. 1 shows the present invention used in cooperation with a hopper in which xerographic toner is batch-stored during manufacture of such toner.

FIG. 1 shows the present invention used in cooperation with a hopper 10 in which xerographic toner is batch-stored during manufacture of the toner. Periodically, valve 11 is opened and toner stored within hopper 10 passes to further process stations, for example final packaging.

While the present invention is described in the environment of toner manufacturing, it is not to be limited thereto since it is only necessary for operation of the present invention that hopper 10 contain material which is flowable through conduit 12 by virtue of subatmospheric pressure within sample container 13. While flow to container 13 is induced by subatmospheric pressure, in the environment of FIG. 1, it is also possible that hopper 10 be maintained at a subatmospheric pressure and that container 13 be at a lower subatmospheric pressure, or perhaps hopper 10 is above atmospheric pressure and container 13 is also above atmospheric pressure, but at a lower atmospheric pressure.

The present invention provides a conduit 14 which is in continuous communication with a source of positive-pressure fluid, represented by arrow 15. This fluid source is preferably gaseous, and may be a high-pressure air or nitrogen source of 120 pounds per square inch (PSI) with a flow capacity of four standard cubic feet per minute (SCFM). If the material to be sampled is explosive, nitrogen is preferred, or other fluid may be used as is required for sample compatibility.

Conduit 14 communicates with T-connection 15A and conduits 16 and 17. Conduit 16 terminates at flow restrictor 18. Flow restrictor 18 operates to produce a source of negative pressure at conduit 19, by virtue of the flow through the restrictor. Specifically, flow restrictor 18 is a venturi.

Flow from source 15 continues through conduit 20 to atmosphere through dust collector 21.

A quantity-of-flow regulator in the form of needle valve 22 connects conduit 17 to conduit 23.

Conduits 19 and 23 terminate at four-port valve 24, this valve having a manual handle 25 which is spring biased to a neutral position, as shown. Handle 25 is manually movable to the positions identified as "1" and "2". In the "1" position conduit 23 is connected to conduit 12 and a flow is established in a direction into hopper 10. This flow is operable to purge conduit 12 of any residual toner left from a previous sample cycle, and the toner adjacent the lower end 26 of conduit 12 is fluidized by this airflow. Needle valve 22 controls the magnitude of this airflow. In addition, handle 25 in the "1" position connects conduit 19 to sample container 13. In a preferred embodiment, sample container 13 is removable from valve 24 and comprises a metal cup of one liter capacity having rigid walls. By virtue of the connection of container 13 to conduit 19, the negative-pressure source established by venturi 18 evacuates container 13 to a subatmospheric pressure. If desired, a meter, not shown, may be provided to read the magnitude of this subatmospheric pressure.

After handle 25 has been held in its "1" position for approximately five seconds, it is immediately moved to its "2" position. In this position, conduit 12 is connected to now-evacuated sample container 13, and fluidized toner adjacent end 26 of conduit 12 flows in an opposite direction to container 13. After approximately five seconds, handle 25 is returned to its neutral position. Container 13 can now be removed for testing, weighing and the like.

Figure 2:
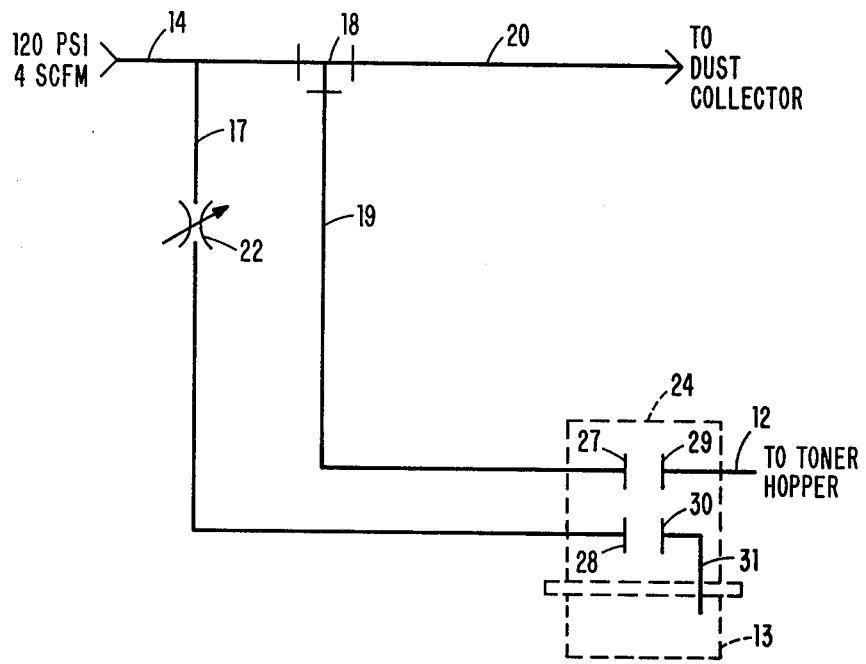
FIG. 2 is a pneumatic schematic diagram of a portion of the pneumatic circuit of FIG. 1, and showing FIG. 1's manual four-port valve in its neutral position.

FIG. 2 is a schematic diagram of the pneumatic apparatus of FIG. 1, wherein the same reference numerals have been used to identify the various components. This figure shows the internal conduits of valve 24, the four valving ports 27-30 contained within the valve, and conduit 31 which connects valve port 30 to container 13. Valve 24 also contains internal conduits which connect valve ports 27, 28, 29 and 30 to conduits 19, 23, 12 and 31, respectively. However, these internal conduits have not been given separate reference numerals.

Figure 3:
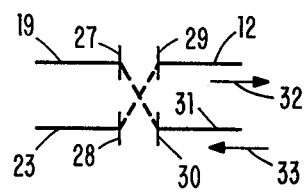
FIG. 3 is the pneumatic schematic diagram of this four-port valve when it has been moved to its number one position.
Figure 4:
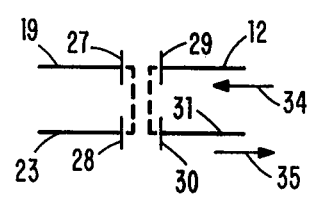
FIG. 4 is the pneumatic schematic diagram of the four-port valve in its number two position.

FIG. 2 shows handle 25 (FIG. 1) in its neutral position, whereas FIGS. 3 and 4 show this handle in the "1" and "2" positions, respectively. As has been explained, with handle 25 in the "1" position, valve port 28 is connected to valve port 29, and thus conduit 23 is connected to conduit 12 to thereby establish a first pneumatic circuit means. An airflow represented by arrow 32 is thus established to conduit 12. This flow purges conduit 12 of any residual toner which may remain from a previous operation of valve 24 in the "2" position.

In addition, valve 24 in the "1" position connects port 27 to port 30 to thereby establish a second pneumatic circuit means. Conduit 19 is now connected to conduit 31, thus inducing airflow through conduit 31 in the direction represented by arrow 33. As was mentioned, this flow through conduit 31 purges this conduit of residual toner which may remain from a previous operation of the valve in its "2" position.

After conduits 12 and 31 have been purged, the toner at end 26 of conduit 12 has been fluidized, and sample container 13 has been evacuated, the valve is moved to its "2" position, shown in FIG. 4. In this position, valve ports 29 and 30 are interconnected, thus connecting the now-purged conduits 12 and 31 in series between toner location 26 and now-evacuated sample container 13 to thereby establish a third pneumatic circuit means. As a result, opposite-direction flow, as represented by arrows 34 and 35, is induced in conduits 12 and 31, respectively, by the subatmospheric pressure in now-evacuated container 13. A sample of fluidized toner now moves to sample container 13.

In valve position "2", valve ports 27 and 28 are interconnected. However, this pneumatic circuit is not critical to operation of the present invention.

After removing sample container 13, one has the option of purging the conduits, prior to taking the next sample. This is accomplished by returning handle 25 to position "1" for five seconds.

Figure 5:
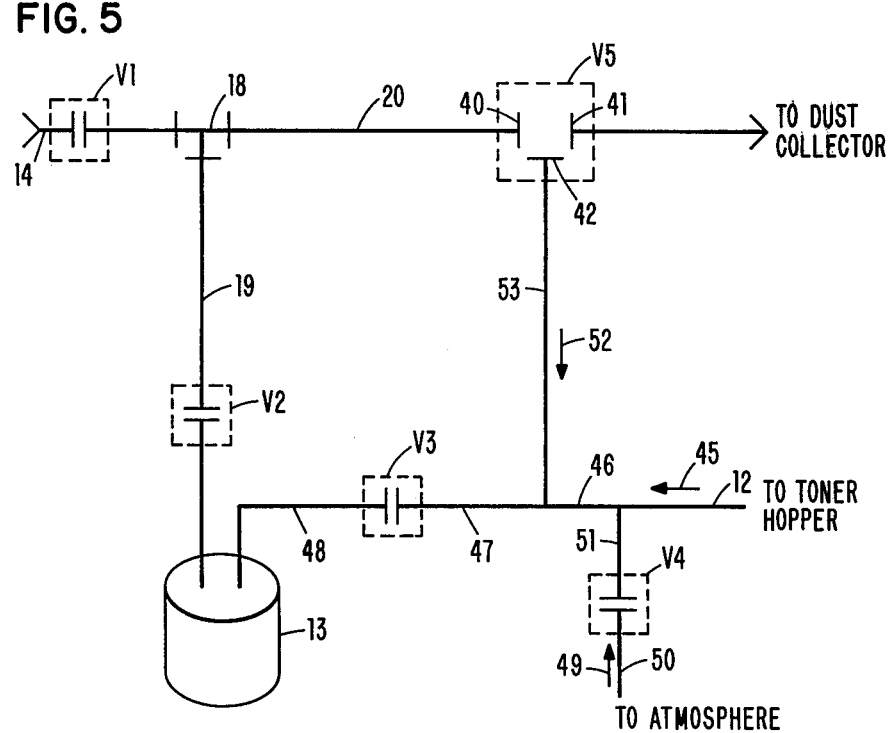
FIG. 5 is a pneumatic schematic diagram of an embodiment of the present invention using a number of separate valves.

FIG. 5 is a schematic diagram of an embodiment of the present invention which uses five discrete valves, rather than a single valve as shown in FIGS. 1-4. In this embodiment, conduit 14 connecting venturi 18 to the source of positive-pressure fluid includes a valve V1. Conduit 19 which connects to the source of negative-pressure established by venturi 18 contains a valve V2. Conduit 20, rather than exiting directly to the dust collector, contains a three-port valve having ports 40, 41 and 42.

Operation of the apparatus of FIG. 5 begins with opening of valve V1, either manually or by an electronic scheduler. Shortly thereafter, valve V2 opens. Valve V5 is deenergized at this time. The construction and arrangement of valve V5 is that in its deenergized state, valve ports 40 and 41 are interconnected. Thus, at this time a negative pressure exists at conduit 19, and with valve V2 open, sample container 13 is evacuated. Approximately five seconds later, valve V2 is deenergized, thus completing the evacuation step. Substantially immediately thereafter, valve V3 opens, thereby causing toner to flow in the direction 45 through conduit 12, conduits 46 and 47, open valve V3 and conduit 48 to sample container 13. After approximately one second of such flow, valve V4 is energized. The opening of valve V4, vents the junction of conduits 12 and 46 to atmosphere, thus terminating flow of toner through conduit 12. Rather, atmospheric air now flows in the direction 49 through conduits 50, open valve V4, conduits 51, 46 and 47, open valve V3 and conduit 48 to container 13. This airflow through conduits 47 and 48 purges the conduits and valve V3 of residual toner from this toner sample period, in preparation for the next sample period.

After approximately two additional seconds, valve V4 is closed, by deenergization thereof.

At substantially the same time, valve V3 is deenergized. About one second later, valve V5 is energized. In the energized state, communication between valve ports 40 and 41 is interrupted, whereas communication is established between valve ports 40 and 42. As a result, positive pressure air flows in the direction 52 through conduit 53 and through conduits 46 and 12 to the toner hopper. This flow purges conduits 46 and 12 of toner accumulated from the current toner sample interval, in preparation for the next sample interval, and also fluidizes toner in the hopper. After a second or so, valve V5 is deenergized, and substantially simultaneous therewith, valve V1 is deenergized, thus completing the sample interval.

In comparing the apparatus of FIG. 2 with that of FIG. 5, it is noted that FIG. 2's conduit 31, which will be called the second conduit portion, is directly purged of residual toner by virtue of airflow induced by the negative-pressure source represented by venturi 18. In FIG. 5, conduit section 48, valve V3 and conduit section 47 comprise a corresponding second conduit portion. In FIG. 5, this second conduit portion is purged of residual toner due to operation of the negative-pressure source formed by venturi 18. However, in this case, the purging is indirect in that venturi 18 first operates to evacuate container 13, and this force is later operable to purge FIG. 5's second conduit portion 47, V3, 48 at the end of a sample interval, when valve V4 opens. Generically, these two modes of operation are considered to be equivalent.

In addition, the purging of FIG. 2's conduit 12, which will be called the first conduit portion, prior to a given sample flow, but during a sample cycle in which that given sample will flow, is considered equivalent to the purging of FIG. 5's equivalent first conduit portion 46, 12 at the end of a sample cycle.

The two embodiments represented by FIGS. 2 and 5 are equivalents in that both provide a first fluid-flow means which is powered by positive-pressure to purge their respective first conduit portions of residual toner. In addition, each has a corresponding second and third fluid-flow means, the second means being powered by negative-pressure and operating to both evacuate the sample container and purge their respective second conduit portions of residual toner, the third fluid-flow means being powered by the evacuated container and comprising the first and second conduit portions connected in series, to cause toner to flow to the container.

More specifically, the first fluid-flow means of FIG. 2 is with valve 24 in position 1 (FIG. 3) where conduit 23 is connected to conduit 12 and positive pressure from conduit 14 purges conduit 12. The corresponding portion of FIG. 5 is the mode of operation wherein valves V2, V3 and V4 are closed, and valve V5 operates to connect 40 to 42. Positive pressure at conduit 14 now purges conduits 46 and 12 by way of flow 52.

The second fluid-flow means of FIG. 2 is also with valve 24 in position 1, where conduit 31 is connected to conduit 19 and negative pressure from fluid restrictor 18 causes a flow to both evacuate sample container 13 and purge conduit 31. The corresponding portion of FIG. 5 comprises two modes of operation. The first mode is accomplished when valve V2 is open as valves V3 and V4 are closed, and as valve V5 operates to connect 40 to 41. The negative pressure from fluid restrictor 18 now evacuates the container. Later, immediately after a toner sample has been gathered, and while negative pressure still remains in the container, valve V4 is opened (as valve V2 is closed, valve V3 is open and valve V5 operates to connect 40 to 41) and the negative container pressure induces flow 49 which purges FIG. 5's second conduit portion 47, V3, 48.

Note that in FIG. 2 the purging of first conduit portion 12 and the purging of second conduit portion 31 occur prior to the collection of a toner sample in the container, whereas in FIG. 5 the purging of first conduit portion 46, 12 and the purging of second conduit portion 47, V3, 48 occur subsequent to the collection of a given toner sample in the container, and thus constitute the required purging operation for the next toner sample to be collected.

Continuing the comparison of FIGS. 2 and 5, the above-mentioned third fluid-flow means of FIG. 2 is with valve 24 in position 2 (FIG. 4) where conduit 29 is series-connected to conduit 31 and the negative pressure within the evacuated sample container causes toner to flow thereto. The corresponding portion of FIG. 5 is the mode of operation in which valves V2 and V4 are closed, valve V3 is open, and valve V5 operates to connect 40 to 41. The two conduit portions 12, 46 and 47, V3, 48 are now connected in series and the negative pressure within the evacuated sample container causes toner to flow thereto.

In some situations it is desirable to automatically sequence FIG. 2's valve 24, and/or collect a composite sample of a number of individual samples collected in sample container 13.

Figure 7:
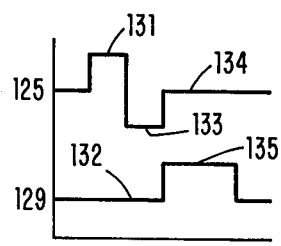
FIG. 7 is a cycling timing diagram of the apparatus of FIG. 6.
Figure 6:
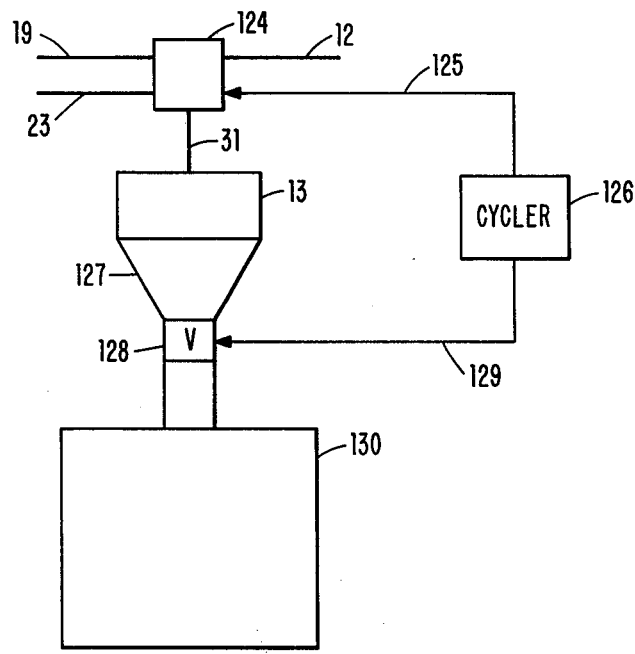
FIG. 6 is an automated version of FIG. 1, in which the four-port valve is automatically cycled, and an additional composite-sample container is provided.

FIGS. 6 and 7 show an embodiment of the present invention which accomplishes both of these results.

In FIG. 6, four-port valve 124 is controlled by the signal on conductor 125 in accordance with the output of electrical cycler 126. Cycler 126 may be, for example, electric motor driving cams which operates switches, as is well known.

Valve 124 is the functional equivalent of FIG. 1's valve 24.

In FIG. 6, conduit 31 is the means by which samples are collected in sample container 13, in the manner above described. Container 13 includes a funnel-shaped bottom 127 which terminates in valve 128. Valve 128 includes an electric actuator (not shown) which is controlled by the signal on cycler output conductor 129. When valve 128 is open, the content of container 23 is gravity-dumped to large composite-sample container 130.

As shown in FIG. 7, when valve 124 is controlled to evacuate sample container 13 (condition 131), valve 128 is closed (condition 132). Valve 128 is also closed when a sample flows to container 13 (condition 133). Thereafter, when valve 124 is in the neutral position (as above defined in connection with FIG. 1's valve 24), this being FIG. 7's condition 134, valve 128 opens (condition 135).

FIG. 7's cycle is repeated a number of times to collect a composite sample within container 130.

Broadly, the present invention comprises a pneumatic sampler which operates to purge the sample-flow conduit of a prior sample residuum, and to use pressure energy stored in the sample container to produce such sample-flow, sequential order of these two functions being as shown in FIG. 2 or as shown in FIG. 5.

While preferred embodiments of the invention have been described, it is to be understood that the present invention is not limited to these precise disclosures, and that the invention is defined by the scope of the appended claims.

What is claimed is:

1. A pneumatic sampler of flowable material operable to cause an amount of such material to flow from a material mass to a sample container, comprising:
   a fluid restrictor adapted to be connected to a source of positive-pressure fluid such that fluid flow through said restrictor produces a source of negative-pressure;
   first pneumatic circuit means, including a first portion, adapted to connect the source of positive-pressure fluid to the material mass to cause flow in a first direction toward the material mass;
   second pneumatic circuit means, including a second portion, adapted to connect the sample container to said source of negative pressure to evacuate the sample container by virtue of flow in a first direction toward said source of negative pressure;
   third pneumatic circuit means including only said first and second portions series connected between the sample container and the material mass to cause material flow in a direction opposite said first direction through said first and second portion, from the material mass to the sample container; and means operable to sequentially effect operation of said first and second pneumatic circuit means, and then operation of said third circuit means.

2. The sampler defined in claim 1 wherein the positive-pressure fluid is a gas, wherein the flowable material is powder-like, wherein said first pneumatic circuit means operates to fluidize the powder, and wherein said third pneumatic circuit means is rendered operable while the powder is in a fluidized state.

3. The sampler defined in claim 1 including means operable to adjust the quantity of flow in said first pneumatic circuit means.

4. The sampler defined in claim 2 including means operable to adjust the quantity of flow in said first pneumatic circuit means.

5. The sampler defined in claim 3 wherein said first and second pneumatic circuit means are simultaneously operable, followed by operation of said third pneumatic circuit means.

6. A pneumatic sampler of flowable material for use in accumulating an amount of such material in a sample container by causing material flow through first and second conduit portions which extend between said container and a mass of such material, comprising:

a fluid restrictor adapted to be connected to a source of positive-pressure fluid such that fluid flow through said restrictor produces a source of negative-pressure;

first fluid-flow means powered by said source of positive-pressure for purging said first conduit portion of residual material;

second fluid-flow means powered by said source of negative-pressure for evacuating said container and purging said second conduit portion of residual material; and third fluid-flow means powered by said evacuated container, and comprising said first and second series connected conduit portions, for causing material to flow from the mass to said container.

7. The pneumatic sampler defined in claim 6 wherein said fluid is a gas, and purging of said first conduit portion and purging of said second conduit portion occur prior to flow of material to said container.

8. The pneumatic sampler defined in claim 7 wherein said fluid is a gas, and purging of said first conduit portion and purging of said second conduit portion occur subsequent to flow of material to said container.

9. A method of pneumatically sampling a flowable material comprising the steps of:

providing a positive-pressure fluid source;

providing fluid-flow powered by said positive-pressure source through venturi-like means so as to generate a negative-pressure source;

providing first and second pneumatic conduit portions which are adapted to be connected in series to establish communication between a source of flowable material and a sample container;

providing first pneumatic circuit means powered by said positive-pressure source, and including said first conduit portion, for purging said first conduit portion of residual flowable material;

providing second pneumatic circuit means powered by said negative-pressure source, and including said container and said second conduit portion, for both purging said second conduit portion of residual flowable material, and for establishing negative-pressure within said container; and providing third pneumatic circuit means powered by the negative-pressure within said container, and including a series connection of said purged first and second conduit portions, for causing flowable material to flow to said container.

10. The method defined in claim 9 wherein the step of providing said second pneumatic circuit produces simultaneous purging of said second conduit portion and establishment of negative-pressure within said container.

11. The method defined in claim 9 wherein the step of providing said second pneumatic circuit produces sequential purging of said second conduit portion and establishment of negative-pressure within said container.

* * * * *